United States Patent [19]

Schmitt

[11] Patent Number: 4,517,128

[45] Date of Patent: May 14, 1985

[54] TWO-TAILED SURFACTANTS HAVING ONE AROMATIC CONTAINING TAIL AND THEIR USE IN CHEMICAL WATERFLOODING

[75] Inventor: Kirk D. Schmitt, Pennington, N.J.

[73] Assignee: Mobil Oil Corporation, New York, N.Y.

[21] Appl. No.: 413,576

[22] Filed: Aug. 31, 1982

[51] Int. Cl.$^3$ .................. C07C 141/02; C07C 143/42
[52] U.S. Cl. ........................... 260/458 C; 260/512 R; 260/457; 252/8.55 D
[58] Field of Search ............... 260/512 R, 458 C, 457

[56] References Cited

U.S. PATENT DOCUMENTS

| | | | |
|---|---|---|---|
| 3,529,040 | 9/1970 | Rinkler et al. | 260/512 R |
| 3,619,123 | 11/1971 | Walz | 260/458 C |
| 3,875,202 | 4/1975 | Steckler | 260/458 C |
| 4,153,575 | 5/1979 | Kalfoglou | 260/512 R |
| 4,233,166 | 11/1980 | Allen | 260/458 C |
| 4,283,321 | 8/1981 | Chakrabarti | 260/512 R |

*Primary Examiner*—Alan Siegel
*Attorney, Agent, or Firm*—Alexander J. McKillop; Michael G. Gilman; Charles J. Speciale

[57] ABSTRACT

(Branched alkyl)-polyethoxyalkyl sulfonates, and similar compounds wherein the alkyl sulfonate moiety is replaced by a sulfate moiety, having an aromatic group on one of the branches of the branched alkyl group are provided. These compounds are surfactants which are particularly useful for chemical waterflooding, especially in high brine environments.

4 Claims, 3 Drawing Figures

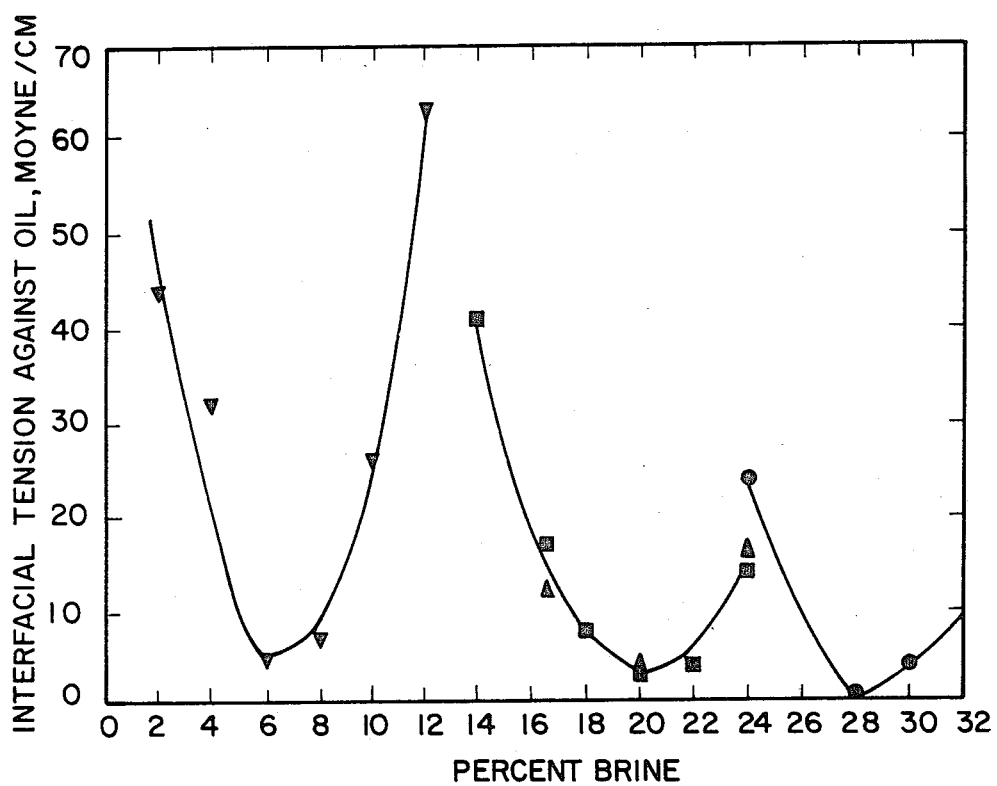
FIG. 1 IFT AGAINST CRUDE OIL AS A FUNCTION OF BRINE CONCENTRATION FOR TWO-TAILED SURFACTANTS

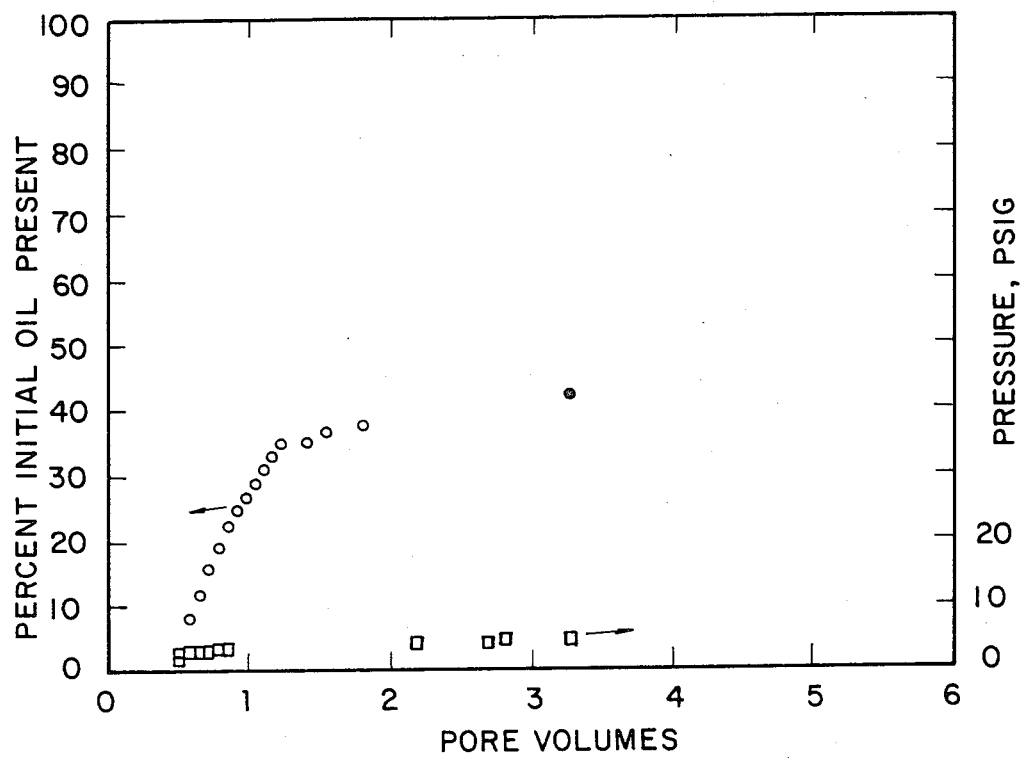
FIG.2 CUMULATIVE OIL RECOVERY VS PORE VOLUME OF FLUID INJECTED USING ONLY A SURFACTANT SLUG.

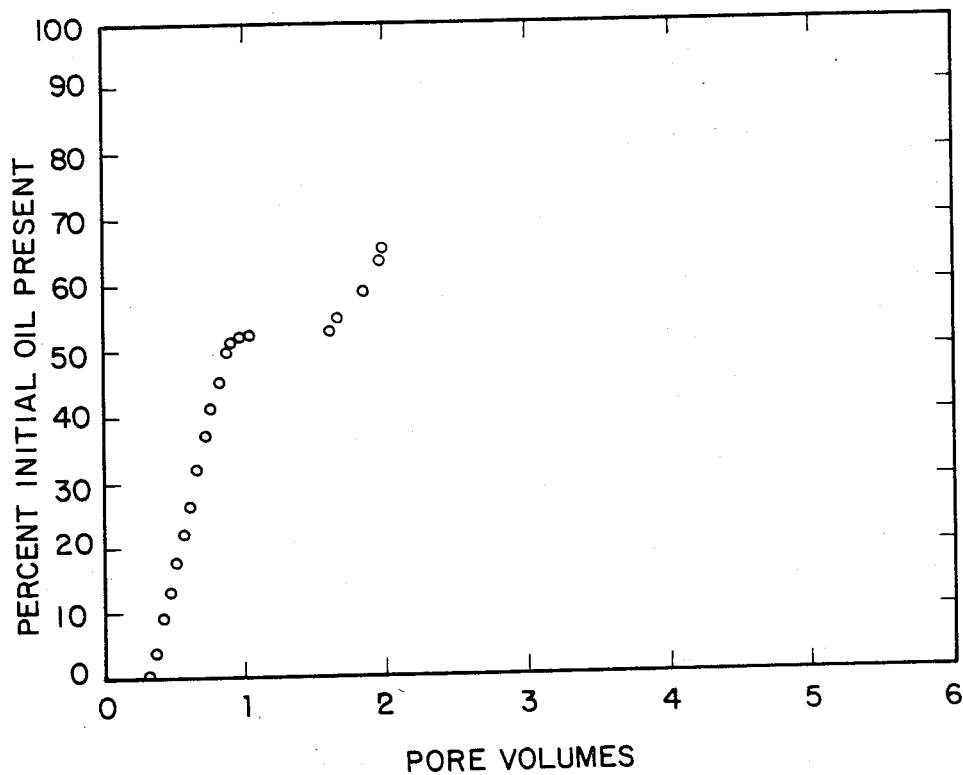
FIG.3 CUMULATIVE OIL RECOVERY VS PORE VOLUMES OF FLUID INJECTED FOR SURFACTANT SLUG FOLLOWED BY THICKENED BRINE.

TWO-TAILED SURFACTANTS HAVING ONE AROMATIC CONTAINING TAIL AND THEIR USE IN CHEMICAL WATERFLOODING

CROSS REFERENCE TO RELATED APPLICATIONS

Copending U.S. patent application Ser. No. 413,591 filed Aug. 31, 1982 in the name of D. H. Hoskin describes low cost, brine tolerant surfactants including, inter alia, 1,3-dialkoxy-2-propoxypolyethoxypropane sulfonates for enhanced oil recovery.

Copending U.S. patent application Ser. No. 373,550, filed Apr. 30, 1982, in the name of Catherine S. H. Chen and Albert L. Williams describes (branched alkyl)-polyethoxypropane sulfonates and their use in enhanced oil recovery. This Chen et al application is a continuation-in-part of U.S. patent applications Ser. No. 259,215 and Ser. No. 259,216, both filed Apr. 30, 1981, and both now abandoned.

Copending U.S. patent application Ser. No. 259,218, filed Apr. 30, 1981, in the name of Kirk D. Schmitt discloses a method for preparing alkylpolyethoxypropane sulfonates. This Schmitt application is, in turn, related to U.S. application Ser. No. 96,947, filed Nov. 23, 1979, in the name of Catherine S. H. Chen, Kirk D. Schmitt and Albert L. Williams, entitled Method of Making Propane Sulfonates, now U.S. Pat. No. 4,267,123.

The above-mentioned United States patent applications and United States patent are expressly incorporated herein by reference.

BACKGROUND

This invention is directed to (branched alkyl)-polyethoxyalkyl sulfonates and similar sulfate compounds having an aromatic group on one of the branches of the branched alkyl group, a process for their preparation and a process for their use in enhancing the secondary or tertiary recovery of oil from subterranean oil deposits or reservoirs, particularly from high salinity reservoirs. In particular, these compounds are suitable as single component surfactants in continuous chemical flooding techniques.

In the recovery of oil from oil bearing deposits it is generally possible to recover only a portion of the original oil by so called "primary methods" which utilize only the natural forces present in the reservoir or deposit. Thus a variety of supplemental techniques have been employed in order to increase the recovery of oil from these subterranean reservoirs. The most widely used supplemental recovery technique is water flooding which involves injection of water into an oil bearing reservoir. However, there are problems associated with the water flooding technique and water soluble surfactants have generally been required to be used for this process to be completely successful. Thus the LTWF (Low Tension Water Flood) method using surfactants which function in low salinity (less then 3 percent) is well known. However, it has been found that preflushing the reservoirs with fresh or low salinity water to reduce the salinity so that the low salinity surfactants of the prior art may be used is not always effective, or, the preflushing is effective only for a short duration and the salinity of the fresh water increases over a period of time since it is in contact with reservoir rocks and clays. Either event renders the low salinity surfactants useless and therefore it is of vital importance to have a surfactant which functions at the salinity of the connant water to negate the necessity of preflushing.

Developments for using surfactants to enhance oil recovery may be categorized according to essentially two different concepts. In the first, a solution containing a low concentration of surfactants is injected into the reservoir. The surfactant is dissolved or dispersed in either water or oil. Large pore volumes (about 15–60% or more) of the liquid are injected into the reservoir to reduce interfacial tension between oil and water and thereby increase oil recovery. Specific relationships exist between interfacial tensions of the oil against the flooding media and the percentage recovery obtained by flooding, i.e., the efficiency of flooding increases as the interfacial tension decreases. Oil may be banked with the surfactant solution process but residual oil saturation at a given position in the reservoir will only approach zero after passage of large volumes of this flooding media.

In the second process, a relatively small pore volume (about 3–20%) of a higher concentration surfactant liquid is injected into the reservoir. The high concentration surfactant liquids displace both oil and water and readily displace all the oil contacted in the reservoir. As the high concentration slug moves in the reservoir, it is diluted by formation flood and the process reverts to a low concentration flood; Enhanced Oil Recovery, Van Poolen & Associates, 1980, Tulsa, Okla.

Aqueous surfactant liquids for injecting into reservoirs contain two essential conponents, namely, water and surfactant. An optional third component may be a hydrocarbon. Such three component mixtures of water, surfactant and hydrocarbon may be in the form of a water-external micellar dispersion as discussed in the Jones U.S. Pat. No. 3,506,071. A cosurfactant fourth component (usually alcohol) can be added. Electrolytes, normally inorganic salts, form a fifth component that may be used.

Work is still in progress in the laboratory and in the field to select the optimum method of injecting surfactant to improve oil recovery. The best process for a specific reservoir is the one which has the potential to provide the greatest efficiency and yield regardless of the concentration level of the surfactant. The chemical system, however, to be efficient must be tailored to the specific reservoir.

The prior art with respect to the use of surfactant polymer floods to recover oil from reservoirs has disclosed that for a given amount of surfactant, a small slug process with a high surfactant concentration is more efficient than a large slug process with a low surfactant concentration. The former produces oil earlier and takes a smaller number of pore volumes to complete oil production. This is a favorable condition. However, it has become evident that fluid dispersion and mixing take place in the reservoirs and the slug intake routine cannot be maintained. Deterioration of the surfactant and the mobility control slug can lead to process failure or at least a reduction in process efficiency. For heterogeneous reservoirs where fluid dispersion and mixing takes place to a greater extent it is desirable if not vital to have a continuous flooding process with a surfacant which can move oil even at very low concentrations.

There has now been discovered certain novel surfactants and their use in a continuous flooding process wherein low concentrations of the novel surfactant alone can be used to increase the oil production during secondary water flooding processes or to recover residual tertiary oil where the reservoirs already have been water flooded.

SUMMARY

The present invention relates to novel surfactants which are (branched alkyl)-polyethoxyalkyl sulfonates, and similar sulfate compounds wherein the alkyl sulfonate moiety is replaced by a sulfate moiety, having an aromatic group on one of the branches of the branched alkyl group, processes for their preparation and processes for their use, particularly at low concentrations in enhanced oil recovery. The enhanced oil recovery process is especially adaptable to high salinity reservoirs, e.g., reservoirs having a salinity of from about 4 to 30%.

This surfactant, in amount effective for the intended purpose can be used as a single component surfactant without the addition of any other component or cosurfactant. However, it may be desirable to use mixtures of two or more of the branched surfactants described herein, or to use the surfactant in combination with a sacrifical agent such as lignin sulfonate.

BRIEF DESCRIPTION OF THE DRAWINGS

FIG. 1 is a graph showing interfacial tension against crude oil as a function of brine concentration for various two-tailed surfactants.

FIGS. 2 and 3 are graphs showing cumulative oil recovery vs pore volume of injected surfactant slug.

DETAILED DESCRIPTION

The surfactants of this invention may have the formula:

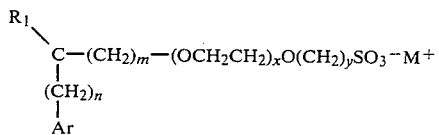

where:
(i) n and m are from 0 to 3;
(ii) y is from 0 to 5, preferably from 0 to 3, most especially 3;
(iii) x is a rational number (e.g. including fractions) from 2 to 8;
(iv) $R_1$ is $C_4$-$C_{10}$ alkyl;
(v) Ar is substituted or unsubstituted phenyl; and
(vi) M is a cation.

Particular examples of Ar when Ar is substituted phenyl include paramethylphenyl and para-tert.-butylphenyl.

It is noted that, when y is 0, the surfactant may be characterized as a sulfate compound, and, when y is 1 or greater, the surfactant may be characterized as an alkyl sulfonate compound.

M is preferably a monovalent cation. Examples of such monovalent cations include ions of alkali metals and nitrogeneous bases. Where M is an alkali metal ion, it may be sodium or potassium. Various nitogeneous bases, including ammonium or quaternary amines, may be employed. Representative alkylammonium ions include methylammonium, ethylammonium, and normal or isopropylammonium ions, and examples of alkanolammonium ions include monoethanolammonium and triethanolammonium ions.

Sulfonates of this invention can be prepared by methods which in themselves are known in the art. One such method involves the reaction of an alkali metal salt of a (branched alkyl) polyethoxy alcohol with propane sultone. This route provides a convenient laboratory synthesis and gives high yields but is not desirable on a large scale for several reasons. Foremost among them are the facts that (1) such a reaction requires multistep synthesis and purification of propane sultone (2) propane sultone is expensive to purify and its overall yield of 80–90% limits the yield in the preparation of propane sulfonates and (3) propane sultone is a known carcinogen. Therefore, processes involving the use of propane sultone must utilize expensive controls to minimize worker exposure but despite such controls its use will always engender some risk.

An alternative method of synthesis which has potential advantages on a commercial scale without the use of propane sultone can be conducted in accordance with the following reaction sequence.

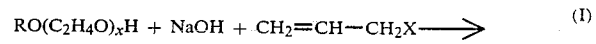
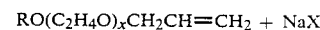
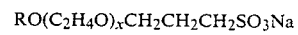

Where R is 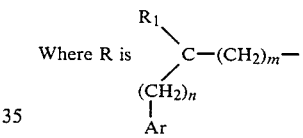

and $R_1$, $R_2$ and x are as defined above and X is halogen or aryl sulfonate (e.g., tosylate).

Where R is such that the allyl ether product of reaction (I) has a solubility in water or less than 0.5% the process can be conducted in two steps in a single reactor without isolation of intermediates in almost 100% yield by control of reaction conditions in steps (I) and (II). Step (I) can be carried out in a completely aqueous system if about 50% NaOH is used as the base and if close contact between the water insoluble allyl halide and alcohol is brought about by inclusion of a certain minimum amount of desired sulfonate final product in the reaction vessel. The initial portion of desired sulfonate final product may be prepared by any suitable conventional route such as e.g., the propane sultone route discussed previously. At the end of the reaction any excess allyl chloride is easily distilled from the reactor. It need not be dried but may be recycled directly, nor must it be separated from an organic solvent since no organic solvent is used.

The preparation of allyl ethers by the reaction of sodium or sodium methoxide with the alcohol followed by reaction with allyl chloride all in an organic solvent such as toluene or tetrahydrofuran (the Williamson ether synthesis) is well known and may be found in many standard textbooks on organic chemistry.

The reaction of $NaHSO_3$ with simple olefins, step (II), has been much studied. The literature teaches that for simple water-soluble olefins or olefins which can be made soluble by the addition of small amounts of alcohols, all that is required for high conversions to the desired products are conditions in which all reagents are dissolved in a single phase.

In the present method of preparation the (branched alkyl) polyethoxy allyl ethers do not behave this way. Conditions may be found in which all the reagents are dissolved in a single phase in alcohol and water and yet conversion will not exceed 40 or 50%. However, when a minor amount of propane sulfonate product is present in the reaction medium the conversion may be as high as 90% or more. Accordingly, it is advantageous to recycle part of the branched alkoxyalkylpolyethoxpropane sulfonate final product of the reaction so that it is present during reaction. In general, the propane sulfonate product is present in a molar ratio of 1:1 to about 1:10 based on the allyl ether.

In Examples 1-6 which follow, there is described the preparation of four surfactants. Examples 1-5 describe the preparation of various intermediates. More particularly, Examples 1-4 describe the preparation of various alcohols, and Example 5 describes the preparation of tetrahydropyran ether of 2-[2-(2-chloroethoxy)ethoxy] ethanol. Example 6 describes the preparation of four surfactants using the intermediates of Examples 1-5.

EXAMPLE 1

Synthesis of 2-benzyl-1-heptanol

Hydrogenation of 40 g α-pentylcinnamaldehyde (Pfaltz and Bauer, Inc.) at 40 psig $H_2$ in 160 ml ethanol over 2 g 10% Pd/C for 30 min. followed by filtering, stripping and fractional distillation yielded 31 g pale yellow oil bp 115-125/0.2 mm which showed a single peak on a 2'×¼" 10% SE-30 GC column temperature programmed from 150° to 270° at 6°/min. Carbon-13 NMR was consistent with the assigned structure.

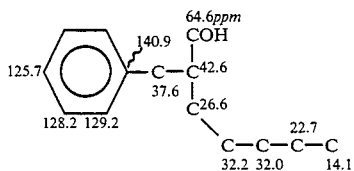

EXAMPLE 2

Synthesis of 2-benzyl-1-nonanol.

The acohol was prepared by hydrogenation of α-heptylcinnamaldehyde exactly as in Example 1. α-Heptylcinnamaldehyde was pepared as follows: To a mixture of 53.8g (0.50 mole) benzaldehyde 50ml ethanol and 25 ml 10% NaOH at reflux were added 56.8 g (0.40 mole) nonanal dropwise over 20 min. Halfway through the addition of nonanal an additional 25 ml 10% NaOH were added. After two hours at reflux the mixture was cooled, diluted with 100 ml 30°-60° petroleum ether, washed once with 50 ml 5% HCl, once with saturated NaCl brine, filtered through 4A molecular sieves, stripped and fractionally distilled, bp 135°-150°/0.15 mm, to give 56.6 g (61%) whose IR showed aromatic CH stretch from 3000-3100 cm $^{-1}$, aldehyde CH at 2705 cm$^{-1}$, and an aldehyde C=O at 1706 cm$^{-1}$.

EXAMPLE 3

Synthesis of 1-phenyl-2-decanol

Glassware was dried overnight at 110°, assembled hot under argon, and thoroughly degassed via three cycles of a Firestone valve before use. All reagent transfers were carried out using double ended needle techniques (See, for example, "Organic Synthesis via Boranes", H. C. Brown, Wiley Interscience, N.Y., N.Y., 1975, page 210).

Thus, to 500 ml 1.4 molar benzyl magnesium chloride in THF (Alpha Inorganics) were added 94.6 g nonanal dropwise, with ice cooling, over 1 hour, the mixture kept 1 hour at room temperature, quenched with 20 ml saturated NaCl brine and 500 ml 5% HCl, stripped, and 500 ml diethyl ether added. The organic phase was washed once with 100 ml $H_2O$, once with 200 ml saturated NaCl brine, filtered through 4A molecular sieve, stripped and fractionally distilled to give 122.1g (78%) water white product bp 111°-113°/0.2 mm whose gas chromatograph on a 10% SP-2100 column programmed from 170° to 270° at 8°/min showed a single peak at 430 sec.

EXAMPLE 4

7-Hydroxymethylpentadecane

For the purposes of comparison, the above 7-Hydroxymethylpentadecane compound was obtained commercially from Pfaltz and Bauer.

EXAMPLE 5

Tetrahydropyran Ether of 2-[2-(2-chloroethoxy)ethoxy]ethanol

The chloroalcohol was freshly distilled from $K_2CO_3$ before use because it contained enough HCl to lead to spontaneous exothermic reaction when mixed with dihydropyran. The alcohol (1.5 mole) and dihydropyran (3.0 mole) were mixed in a 3 l E flask, 2.9 l $CH_2Cl_2$ added followed by 20 g 4A molecular sieves and 0.18 mole pyridinium p-toluenesulfonate. After stirring overnight the reaction was washed once with 200 ml 50% $K_2CO_3$, filtered, washed once with 200 ml 50% $K_2CO_3$, once with 100 ml saturated NaCl, filtered through 4A sieves and distilled. HPLC confirmed the crude product contained 3% alcohol. The yield was 92% of material bp 70°-80°/1.5 mm Hg.

EXAMPLE 6

Addition of Sodium Triethyleneoxypropane Sulfonate Group to Alcohols

A mixture of 350 ml xylene and 0.500 mole of each of the alcohols of Examples 1-4 was degassed via three cycles of a Firestone valve, refluxed to dryness through a Dean-Stark trap, cooled to 15° in ice and 325 ml 1.6 M butyllithium in hexane (Aldrich Chemical Co.) added in 20 minutes followed by 125 ml of the tetrahydropyranyl ether of 2-[2-(2-chloroethoxy)ethoxy] ethanol (Example 5). The hexane was distilled through a Claisen head until the overhead reached 128° then refluxed overnight, cooled to room temperature, quenched with 175 ml saturated NaCl brine plus 80 ml $H_2O$, diluted with ether and the phases separated. The organic phase was washed twice with 60 ml $H_2O$, once with 175 ml saturated NaCl brine, filtered through 4A molecular sieves and stripped. The residue was dissolved in 700 ml ethanol, 37 g pyridinium p-toluenesulfonate (J. T. Baker Chem. Co.) added, the mixture refluxed 4 hours, cooled, neutralized with 12 g potassium hydroxide in 35 ml $H_2O$, stripped, partitioned between 750 ml ether and 200 ml $H_2O$. The ether layer was washed once with 90 ml saturated NaCl brine, filtered through 4A molecular sieves, stripped, rapidly distilled on a Kugelrohr then fractionally redistilled. The yield of triethoxylated alcohol at this point ranged from 0.18-0.25 mole (36-50%). The alcholol was dissolved in 4 volumes toluene, degassed via three cycles of a Firstone valve, refluxed to dryness through a Dean-Stack trap, metallic sodium (96% of theory.) added over 10-20 min, reflux, continued until all the sodium dissolved, the mixture cooled to room temperature, then freshly distilled propane sultone (Aldrich Chemical Co. or Eastman) added in 20 min. After 1 hour at room temperature the solvent was removed in vacuo and the product recrystallized once from an acetone/methanol mixture to give 0.11-0.15 mole final product. Carbon-13 NMR peaks characteristic of the sodium triethyleneoxypropane sulfonate group were invariably found as follows:

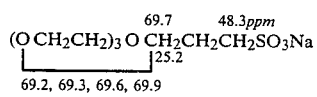

The four surfactants prepared according to the foregoing Examples may be represented as follows:

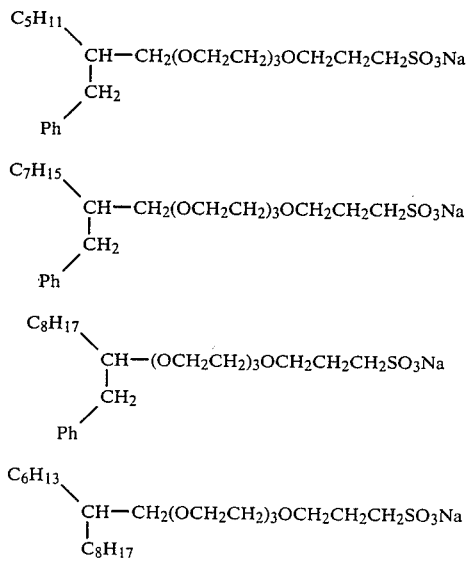

EXAMPLE 7

Measurements of Interfacial Tensions

The above represented compounds 2-4 each have a total number of 16 carbon atoms in the hydrophobic tail.

Interfacial tensions (IFT) against West Burkburnett crude oil were measured for 0.1% solutions of each of the surfactants in a synthetic brine containing NaCl, $MgCl_2$, and $CaCl_2$ in weight ratio 18.3:1:3.63 with total dissolved solids content expressed as "% brine". The spinning drop technique [J. L. Cayias, R. S. Schecter, W. H. Wade; *Adsorption at Interfaces*, Symposium Ser. #8, ACS, 234 (1975)] was used to measure IFT.

Table 1 and FIG. 1 show the results for the three sixteen carbon hydrophobe surfactants and fourteen carbon hydrophobe surfactants of Example 6. It is evident that a two-tailed surfactant is much more brine tolerant, for the same hydrophilic head, if one of the tails incorporates an aromatic group than if both tails are aliphatic.

TABLE 1

Interfacial Tension at Different Salinities
IFT Against Crude Oil, mdyne/cm

| % Brine | Surfactant[a] 1 | 2 | 3 | 4 |
|---|---|---|---|---|
| 30 | 4.3 | | | |
| 28 | 0.4 | | | |
| 24 | 24 | 14 | 16 | |
| 22 | | 4 | 4 | |
| 20 | | 2.9 | 4 | |
| 18 | | 7.8 | 8 | |
| 16.6 | | 17 | 12 | |
| 14 | | 41 | 41 | |
| 12 | | | | 63 |
| 10 | | | | 26 |
| 8 | | | | 7 |
| 6 | | | | 5 |
| 4 | | | | 32 |
| 2 | | | | 44 |

[a] Surfactant Concentration = 0.1%

EXAMPLE 8

Measurement of Interfacial Tension

To show probable efficacy for oil recovery at very low concentrations, such as stripping type enhanced oil recovery process, the IFT against crude oil was measured at 100 ppm surfactant concentration (Table 2). IFT's of 10 mdyne/cm or less are easily achieved over a broad range of concentrations. Since it is generally agreed [L. M. Prince; "Microemulsions", Academic Press, New York, 1977, pg 153] that IFT's of 10 mdyne/cm or less are sufficient to mobilize substantial amounts of oil from reservoir rocks, it is evident that injection of low concentrations of these surfactants will increase oil recovery.

TABLE 2

Interfacial Tension Against Oil at Different Salinities
IFT, mdyne/cm

| % Brine | Surfactant[a] 1 | 2 | 3 |
|---|---|---|---|
| 30 | 2.8 | | |
| 28 | 5.5 | | |
| 24 | 28 | 59 | 58 |
| 22 | | 6.5 | 6.4 |
| 20 | | 3.3 | 2.7 |
| 18 | | 6.0 | 1.6 |
| 16.6 | | 11 | 7.9 |
| 14 | | 29 | 29 |

[a] Surfactant Concentration = 100 ppm

EXAMPLE 9

Measurement of Interfacial Tension

An alternative way to measure the lowering of IFT between oil and water is to measure the amount of oil solubilized into a middle phase when oil and water are equilibrated in contact with one another. Solubilization is defined as the volume of oil in the middle phase divided by the volume of surfactant in the middle phase. Equal volumes of crude oil and surfactant solution were shaken and allowed to euilibrate at least one month (Table 3).

TABLE 3

| | Solubilization by Surfactant 2 | | |
|---|---|---|---|
| % Brine | % 2-BuOH | Solubilization at 25° C. | 50° C. |
| 21 | 0 | 0 | 0 |
| 18 | 0 | 5.1 | 23 |
| 15 | 0 | 2.8 | 9.4 |
| 12 | 0 | 1.4 | 9.4 |
| 21 | 1 | 0.5 | 0 |

TABLE 3-continued

| % Brine | % 2-BuOH | Solubilization at 25° C. | 50° C. |
|---|---|---|---|
| | | Solubilization by Surfactant 2 | |
| 18 | 1 | 2.8 | 23 |
| 15 | 1 | .9 | 15 |
| 12 | 1 | 2.3 | 5.6 |
| 21 | 2 | 0.5 | 0 |
| 18 | 2 | 23 | 1.9 |
| 15 | 2 | 3.3 | 8 |
| 12 | 2 | 1.9 | 22 |

Solubilization in excess of 5 is considered sufficient to mobilize substantial oil from reservoir rocks. Table 3 indicates that solubilizations greater than 5 exist for a wide range of surfactant/alcohol/brine compositions. Solublizations for surfactant 2 at 12 and 15% brine at 50° and at 18% brine at 25° exceed 5 at all alcohol concentrations indicating that the surfactant's ability to mobilize oil in a slug process will not be jeopardized by chromatographic separation of alcohol and surfactant.

The exact concentration and temperature at which high solubilizations are obtained can be altered by methods known in the art, namely, varying the number of ethyleneoxy groups or the length of the alkyl chain.

EXAMPLE 10

Oil Recovery.

To demonstrate the ability of surfactants of the present invention to recover oil from reservoir rock a 1" by 1" core of 600 m Darcy Berea sandstone was flooded at 25° C. to residual oil content with 18% brine. A 0.20 pore volume slug containing 5% of surfactant 2 and 3% 2-BuOH in 18% brine was injected followed by continuous injection of 18% brine. Thirty percent of the residual oil was produced within one pore volume of the start of injection. The pressure increased 1.5 psig indicating no deleterious viscous phases were formed. The cumulative production of oil as a function of pore volumes of injected fluid is depicted in FIG. 2.

EXAMPLE 11

Oil Recovery

It is known [L. A. Wilson, Jr.; in "Improved Oil Recovery by Surfactant and Polymer Flooding", D. O. Shah and R. S. Schechter, ed., Academic Press, 1976, pg 3] that injection of a thickened water slug following a surfactant slug increases the oil recovery efficiency of the surfactant slug. To demonstrate the compatibility of surfactants of the present invention with this process, a 1" by 12" 600 m Darcy Berea sandstone core was flooded to residual oil saturation at 50° C. with 15% brine. A 0.17 pore volume slug containing 5% of surfactant 2 and 1.5% 2-BuOH (28 cp) was injected followed by continuous injection of a 300 ppm solution of Polytran [Obtained from Jetco Chemicals, Corsicana, Texas as "Actigum CS-11-L"] in 10% brine (11 cp). FIG. 3 shows the cumulative production of residual oil as a function of pore volumes of fluid injected. The residual oil recovery was increased from 30% at one pore volume in Example 10 to 50% with 66% of the residual oil recovered by two pore volumes.

The compounds of the present invention are felt to be novel surfactants with extreme salt and divalent ion tolerance which produce low IFT against oil over a wide range of temperatures, salt concentrations, and alcohol concentrations. These properties make these compounds suitable for use in many types of chemical waterflooding oil recovery processes contemplated in the literature. They are effective in high concentration slugs with and without alcohol or petroleum sulfonate consurfactants, with and without polymeric water thickeners, and with and without sacrificial chemicals such as lignosulfonates [Note G. Kalfoglou, U.S. Pat. No. 4,157,115, June 5, 1979].

High concentration slugs of these surfactants with or without added alcohol are moderately viscous which, in itself, is considered beneficial to oil recovery [W. B. Gogarty and J. A. Davis, Jr. SPE Paper No. 3806, Apr. 16–19, 1972].

Very low concentrations of these surfactants have IFT against oil low enough to indicate they will effectively recover oil when injected in a continuous fashion in concentrations from 10 to 500 ppm.

The compounds of the present invention can be synthesized easily and inexpensively by methods well known in the art.

What is claimed is:

1. A compound of the formula

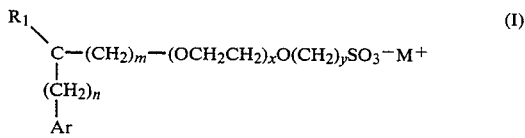

where:
(i) n and m are from 0 to 3;
(ii) y is from 0 to 5;
(iii) x is a rational number from 2 to 8;
(iv) $R_1$ is $C_4$–$C_{10}$ alkyl;
(v) Ar is substituted or unsubstituted phenyl; and
(vi) M is a cation.

2. A compound according to claim 1, wherein said substituted phenyl is para-methylphenyl or para-tert 1-butylphenyl.

3. A compound according to claim 1, wherein y is from 0 to 3.

4. A compound according to claim 1, wherein:
(a) y is 3;
(b) Ar is unsubstituted phenyl; and
(c) M is Na.

* * * * *